(12) United States Patent
Ren et al.

(10) Patent No.: US 9,366,645 B2
(45) Date of Patent: Jun. 14, 2016

(54) MATERIALS AND METHODS FOR DETECTING TOXINS, PATHOGENS AND OTHER BIOLOGICAL MATERIALS

(71) Applicant: UNIVERSITY OF FLORIDA RESEARCH FOUNDATION, INC., Gainesville, FL (US)

(72) Inventors: Fan Ren, Gainesville, FL (US); Stephen John Pearton, Gainesville, FL (US); Tanmay P. Lele, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 131 days.

(21) Appl. No.: 14/148,945

(22) Filed: Jan. 7, 2014

(65) Prior Publication Data

US 2014/0127675 A1    May 8, 2014

Related U.S. Application Data

(62) Division of application No. 12/664,022, filed as application No. PCT/US2009/063502 on Nov. 6, 2009, now abandoned.

(60) Provisional application No. 61/111,977, filed on Nov. 6, 2008.

(51) Int. Cl.
*G01N 27/327* (2006.01)
*G01N 33/543* (2006.01)
*G01N 33/569* (2006.01)
*G01N 27/414* (2006.01)

(52) U.S. Cl.
CPC ........ *G01N 27/3275* (2013.01); *G01N 27/4145* (2013.01); *G01N 33/54373* (2013.01); *G01N 33/56911* (2013.01); *G01N 33/56983* (2013.01); *G01N 2333/33* (2013.01)

(58) Field of Classification Search
CPC .......... G01N 27/3275; G01N 27/4145; G01N 33/56911; G01N 33/54373; G01N 33/56983
See application file for complete search history.

(56) References Cited

U.S. PATENT DOCUMENTS

| | | | |
|---|---|---|---|
| 4,734,750 A | 3/1988 | Okamura et al. | |
| 6,287,776 B1 | 9/2001 | Hefti | |
| 6,338,968 B1 | 1/2002 | Hefti | |
| 6,485,905 B2 | 11/2002 | Hefti | |
| 6,534,801 B2 | 3/2003 | Yoshida | |
| 7,403,113 B2 | 7/2008 | Moon et al. | |
| 2003/0138872 A1* | 7/2003 | Kawasaki | C12Q 1/26 435/25 |

(Continued)

OTHER PUBLICATIONS

Kang, B. S. et al., "Electrical detection of biomaterials using AlGaN/GaN high electron mobility transistors," Journal of Applied Physics, 2008, 031101 pp. 1-11, vol. 104.

(Continued)

*Primary Examiner* — Melanie Y Brown
(74) *Attorney, Agent, or Firm* — Saliwanchik, Lloyd & Eisenschenk

(57) ABSTRACT

Embodiments of the present invention provide binding molecule-functionalized high electron mobility transistors (HEMTs) that can be used to detect toxins, pathogens and other biological materials. In a specific embodiment, an antibody-functionalized HEMT can be used to detect botulinum toxin. The antibody can be anchored to a gold-layered gate area of the HEMT through immobilized thioglycolic acid. Embodiments of the subject detectors can be used in field-deployable electronic biological applications based on AlGaN/GaN HEMTs.

5 Claims, 3 Drawing Sheets

(56) References Cited

U.S. PATENT DOCUMENTS

| | | | |
|---|---|---|---|
| 2005/0014178 A1 | 1/2005 | Holm-Kennedy | |
| 2005/0263790 A1* | 12/2005 | Moon | G01N 33/0075 257/194 |
| 2006/0088839 A1 | 4/2006 | Matsui et al. | |
| 2006/0228723 A1 | 10/2006 | Bradley et al. | |
| 2008/0069971 A1 | 3/2008 | Keersmaecker et al. | |
| 2008/0283875 A1* | 11/2008 | Mukasa | B82Y 10/00 257/253 |

OTHER PUBLICATIONS

Wang, H. T. et al., "Electrical detection of kidney injury molecule-1 with AlGaN/GaN high electron mobility transistors," Applied Physics Letters, 2007, 222101 pp. 1-3, vol. 91.

Kang, B. S. et al., "Prostate specific antigen detection using AlGaN/GaN high electron mobility transistors," Applied Physics Letters, 2007, 112106 pp. 1-3, vol. 91.

Chen, K. H., "c-erbB-2 sensing using AlGaN/GaN high electron mobility transistors for breast cancer detection," Applied Physics Letters, 2008, 192103 pp. 1-3, vol. 92.

Kang, B. S. et al., "Electrical detection of immobilized proteins with ungated AlGaN/GaN high-electron-mobility Transistors," Applied Physics Letters, 2005, 023508 pp. 1-3, vol. 87.

Kang, B. S. et al., "Electrical detection of deoxyribonucleic acid hybridization with AlGaN/GaN high electron mobility transistors," Applied Physics Letters, 2006, 122102 pp. 1-3, vol. 89.

Wang, Y.-L. et al., "Real-time detection of botulinum toxin with AlGaN/GaN high electron mobility transistor," The Electrochemical Society, 215th ECS Meeting, Abstract #884.

U.S. Appl. No. 12/724,117, Claims, filed Mar. 15, 2010.

Wang, Y.-L. et al., "Botulinum toxin detection using AlGaN/GaN high electron mobility transistors," Applied Physics Letters, 2008, 262101 pp. 1-3, vol. 93.

\* cited by examiner

MATERIALS AND METHODS FOR DETECTING TOXINS, PATHOGENS AND OTHER BIOLOGICAL MATERIALS

CROSS-REFERENCE TO RELATED APPLICATIONS

This application is a divisional of U.S. application Ser. No. 12/664,022, filed Dec. 10, 2009, which is the national stage application of International Patent Application No. PCT/US2009/063502, filed Nov. 6, 2009, which claims priority to U.S. Provisional Application Ser. No. 61/111,977, filed Nov. 6, 2008, the disclosures of which are hereby incorporated by reference in their entirety.

BACKGROUND OF INVENTION

Biological weapons are particularly attractive tools for terror because biological agents are available and easy to manufacture, small amounts are required to cause large-scale effects, and attacks can easily overwhelm existing medical resources. Reliable detection of biological agents in the field and in real time has proved to be challenging.

Toxins such as ricin, botulinum toxin or enterotoxin B are environmentally stable, can be mass-produced and do not need advanced technologies for production and dispersal. Clostridium botulinum neurotoxins are among the more deadly toxins and are listed as a National Institute of Allergy and Infectious Diseases (NIAID)—Category A agent for bioterrorism potential. According to Arnon et al. in "Botulinum Toxin as a Biological Weapon" (JAMA, Vol. 285, No. 8, pp. 1059-1070, 2001) and Greenfield et al. in "Microbiological, Biological, and Chemical Weapons of Warfare and Terrorism" (Am. J. Med. Sci., Vo. 323, No. 6, pp. 326-340, 2002), the lethal dose in unvaccinated humans is estimated at 1 ng/kg. Conventional methods of detection involve the use of high performance liquid chromatography (HPLC), mass spectrometry and colorimetric Enzyme-Linked ImmunoSorbent Assays (ELISAs); but these are impractical because such tests can only be carried out at centralized locations, and are too slow to be of practical value in the field. Another test for botulinum toxin detection is the 'mouse assay,' which relies on the death of mice as an indicator of toxin presence. Clearly, such a method is slow and impractical in the field.

A significant issue is the absence of a definite diagnostic method and the difficulty in differential diagnosis from other pathogens that would slow the response in case of a terror attack. This is a critical need that has to be met to have an effective response to terrorist attacks.

In addition to diagnostic methods for biological weapons applications, infectious diseases at hospitals and clinics require reliable and fast detection. Early detection of infectious diseases may be used to treat or prevent a disease or condition.

Methicillin Resistant Staphylococcus Aureus (MRSA) is a type of bacteria that is resistant to many antibiotics, thus fueling its spread in hospitals and healthcare facilities in which people have weakened immune systems. MRSA is very costly and time consuming to treat. In fact, the government estimates the annual costs of treating MRSA to be over four billion dollars. Due to the nature of the fast spreading bacteria, it is imperative to diagnose and begin treatment and isolation as soon as possible.

Unfortunately, the current "gold standard" for MRSA testing is culturing a sample in a lab, and although this is fairly reliable, it typically takes two to three days. Culturing is very time consuming and costs between $8 and $11 per culture. Therefore, an accurate, but faster, technique for detecting these bacteria is needed.

BRIEF SUMMARY

The present invention provides high electron mobility transistors (HEMT) sensors that accurately and rapidly detect biological materials. The sensors of the subject invention can detect, for example, toxins, other antigens, and pathogens. In an embodiment that is specifically exemplified herein, the HEMT sensor of the subject invention can be used for the detection of botulinum toxin.

In specific embodiments, the present invention provides antibody-functionalized HEMT sensors that can be used to detect proteins, including toxins and various protein markers associated with bacterial and viral pathogens.

According to one implementation, a medical diagnostic and/or detection instrument is provided that enables the identification of biological material from fluid samples by an HEMT-based sensor response when a target molecule binds to a binding agent immobilized on the gate region of a HEMT. Preferably, the target molecule is a protein and the binding agent is an antibody or antibody fragment.

In one embodiment, a system is provided that comprises multiple HEMT-based sensors for analyzing samples for analyte content. The system may further comprise an electronic processor for controlling the sensors and/or having them communicate with monitoring and processing electronics.

The system of the subject invention can be incorporated into a handheld device where, for example, the sensors are configured within a removable sensor cartridge. A cartridge reader, user interface, and fluidic interface for sample delivery across cartridge sensors can be provided within a housing configured to receive the cartridge. The electronic processor and the monitoring and processing electronics may be disposed within the housing.

In one embodiment of the invention, an Au-coated gate area of a HEMT is functionalized with an antibody that binds with a botulinum toxin.

According to another embodiment, the subject HEMT-based device serves as a fast and reliable method for screening and testing for hospital acquired infections (HAIs) such as MRSA.

The subject invention further provides methods for using the sensors and systems described herein.

BRIEF DESCRIPTION OF DRAWINGS

FIGS. 1A and 1B show a cross-sectional view of an AlGaN/GaN HEMT sensor according to an embodiment of the present invention.

FIG. 2 shows a plot of I-V characteristics of an AlGaN/GaN HEMT sensor according to an embodiment of the present invention before and after exposure to 100 ng/ml botulinum toxin.

FIG. 3 shows a plot of drain current of an AlGaN/GaN HEMT sensor according to an embodiment of the present invention versus time for botulinum toxin from 0.1 ng/ml to 100 ng/ml.

FIG. 4 shows a plot of drain current of a botulinum toxin sensor according to an embodiment of the present invention versus different concentrations from 0.1 ng/ml to 100 ng/ml of botulinum toxin.

FIG. 5 shows a plot of drain current over time for a botulinum toxin sensor according to an embodiment of the present invention after being washed with PBS in pH 5 to refresh the sensor.

DETAILED DISCaLOSURE

The present invention provides high electron mobility transistors (HEMT) capable of quickly and accurately detecting biological materials. In a specific embodiment, the sensor can detect a botulinum toxin.

In one embodiment of the invention, the subject sensor can be utilized in Homeland Security applications. Further embodiments can be utilized in fish/shellfish farming industries and National Institute of Health (NIH) compact wireless applications. In another embodiment of the invention, the sensor of the subject invention can be utilized as a medical diagnostic and/or detection instrument.

In preferred embodiments, the sensors of the present invention are reliable, inexpensive, highly sensitive, hand-held sensors with response times on the order of a few seconds, which can be used in the field for detecting biological materials.

Specific embodiments of the present invention provide antibody-functionalized HEMT devices for botulinum toxin sensing. According to one embodiment of the invention, an antibody to a botulinum toxin is provided on a gate of the HEMT. The gate of the HEMT can be formed of gold (Au) and functions as a sensing region of the HEMT. In a specific embodiment, the antibody can be attached to the gold gate of the HEMT through thioglycolic acid.

In alternative embodiments, the analyte can be other biological toxins, such as, for example, ricin or enterotoxin B. The analyte can also be a marker associated with bacterial or viral pathogens.

In further embodiments, anthrax (*Bacillus anthracis*), plague (*Yersinia pestis*), smallpox (variola major), tularemis (*Francisella tularensis*), and viral hemorrhagic fevers including filoviruses and arenaviruses can be detected using binding molecules for such agents. Furthermore, other biological agents may be detected.

In another embodiment, such as for medical applications, the HEMT can be functionalized with binding molecules for pathogens including, but not limited to, nosocomal infections such as MRSA, pneumonia, *Pseudomonas aeroginosa*, *Acinetobacter baumannii*, *Stenotrophomonas maltophilia*, *Clostridium difficile*, tuberculosis, urinary tract infection, gastroenteritis, Vancomycin-resistant enterococcus, and legionella.

In one embodiment, a single chip can provide multiple sensors functionalized with antibodies, or other binding molecules, for a plurality of analytes.

The binding molecule of the subject invention is preferably an antibody, or an antibody fragment. Other binding molecules that can be used according to the subject invention include, but are not limited to, polynucleotides (DNA or RNA) and aptamers. The analyte is preferably a protein, but may also be, for example, a polynucleotide.

An antibody used in the present invention can be in any of a variety of forms, including a whole immunoglobulin, an antibody fragment such as Fv, Fab, and similar fragments, as well as a single chain antibody that includes the variable domain complementarity determining regions (CDR), and similar forms, all of which fall under the broad term "antibody," as used herein.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment of an antibody yields an F(ab')$_2$ fragment that has two antigen binding fragments, which are capable of cross-linking antigen, and a residual other fragment (which is termed pFc'). Additional fragments can include diabodies, linear antibodies, single-chain antibody molecules, and multispecific antibodies formed from antibody fragments. As used herein, "antigen binding fragment" with respect to antibodies, refers to, for example, Fv, F(ab) and F(ab')$_2$ fragments. Of particular importance for binding are the first 110 to 130 amino acids at the N-terminus of the amino acid sequences. Thus, high identity in the N-terminus 110, 115, 120, 125, or 130 amino acids constituting the variable region is preferred. Variant sequences preferably have more than 75%, 90%, or even 95% identity in this region.

The subject invention further comprises fusion constructs wherein the antibody, or fragment thereof, may be fused to one or more additional entities. The additional entity(ies) may be, for example, linkers. In this context the binding portion may consist or consist essentially of the antibody. By "consists essentially" it is meant that no other entity is present that substantially effects the ability of the antibody (or fragment thereof) to bind to its target.

"Specific binding" or "specificity" refers to the ability of an antibody or other agent to detectably bind an epitope presented on an antigen, while having relatively little detectable reactivity with other proteins or structures. Specificity can be relatively determined by binding or competitive binding assays, using, e.g., Biacore instruments. Specificity can be exhibited by, e.g., an about 10:1, about 20:1, about 50:1, about 100:1, 10.000:1 or greater ratio of affinity/avidity in binding to the specific antigen versus nonspecific binding to other irrelevant molecules.

"Selectivity" refers to the preferential binding of a protein to a particular region, target, or peptide as opposed to one or more other biological molecules, structures, cells, tissues, etc. For example, selectivity can be determined by competitive ELISA or Biacore assays. The difference in affinity/avidity that marks selectivity can be any detectable preference (e.g., a ratio of more than 1:1.1, or more than about 1:5, if detectable.

Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

Single chain antibody ("SCA") is defined as a genetically engineered molecule containing the variable region of the light chain ($V_L$) and the variable region of the heavy chain ($V_H$) linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. For a review of sFv fragments, see Pluckthun in The Pharmacology of Monoclonal Antibodies, vol. 113, Rosenburg and Moore eds. Springer-Verlag, N.Y., pp. 269 315 (1994).

If desired, the antibodies can be modified. For example, the binding affinity of the antibodies can be increased via various methods known in the art. For example, binding characteristics can be improved by direct mutation, methods of affinity maturation, phage display, or chain shuffling within the nucleic acids encoding the antibody molecules. For example, individual residues or combinations of residues can be randomized so that in a population of otherwise identical antigen binding sites, all twenty amino acids are found at particular positions. Binding characteristics can also be improved by methods of affinity maturation. (See, e.g., Yang et al. (1995) *J. Mol. Bio.* 254, 392-403; Hawkins et al. (1992) *J. Mol. Bio.* 226, 889-896; or Low et al. (1996) *J. Mol. Bio.* 250, 359-368). Methods known in the art include, for example, affinity maturation by VH and VL domain shuffling (described by Marks et al., *Bio/Technology*, 10:779-783 (1992)) and random mutagenesis of CDR and/or framework residues (such as described by Barbas et al., *Proc. Natl. Acad. Sci., USA* 91:3809-3813 (1994); Schier et al., *Gene*, 169:147-155 (1995); Yelton et al. *J. Immunol.*, 155:1994-2004 (1995); Jackson et al., *J. Immunol.*, 154(7):3310-3319 (1995); and Hawkins et al., *J. Mol. Biol.*, 226:889-896 (1992)).

Antibodies within the scope of the invention can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

The AlGaN/GaN HEMT is an exemplary HEMT that can be used according to the subject invention for sensing biological materials. AlGaN/GaN HEMTs have a high electron sheet carrier concentration channel induced by piezoelectric polarization of the strained AlGaN layer. Electrons in the two-dimensional electron gas (2DEG) channel are located at the interface between the AlGaN layer and GaN layer. In addition, there are positive counter charges at the HEMT surface layer induced by the electrons located at the 2DEG channel. Slight changes in the ambient environment can affect the surface charge of the HEMT, thus changing the 2DEG concentration in the channel.

HEMTs can operate over a broad range of temperatures and form the basis of next-generation microwave communication systems. Accordingly, embodiments of the present invention can be implemented as an integrated sensor/wireless chip.

The HEMT sensor can provide a fast response time. In one embodiment, the subject device can be used as a wireless based sensor to send test results to a display or separate device.

Figures 1A, 1B:
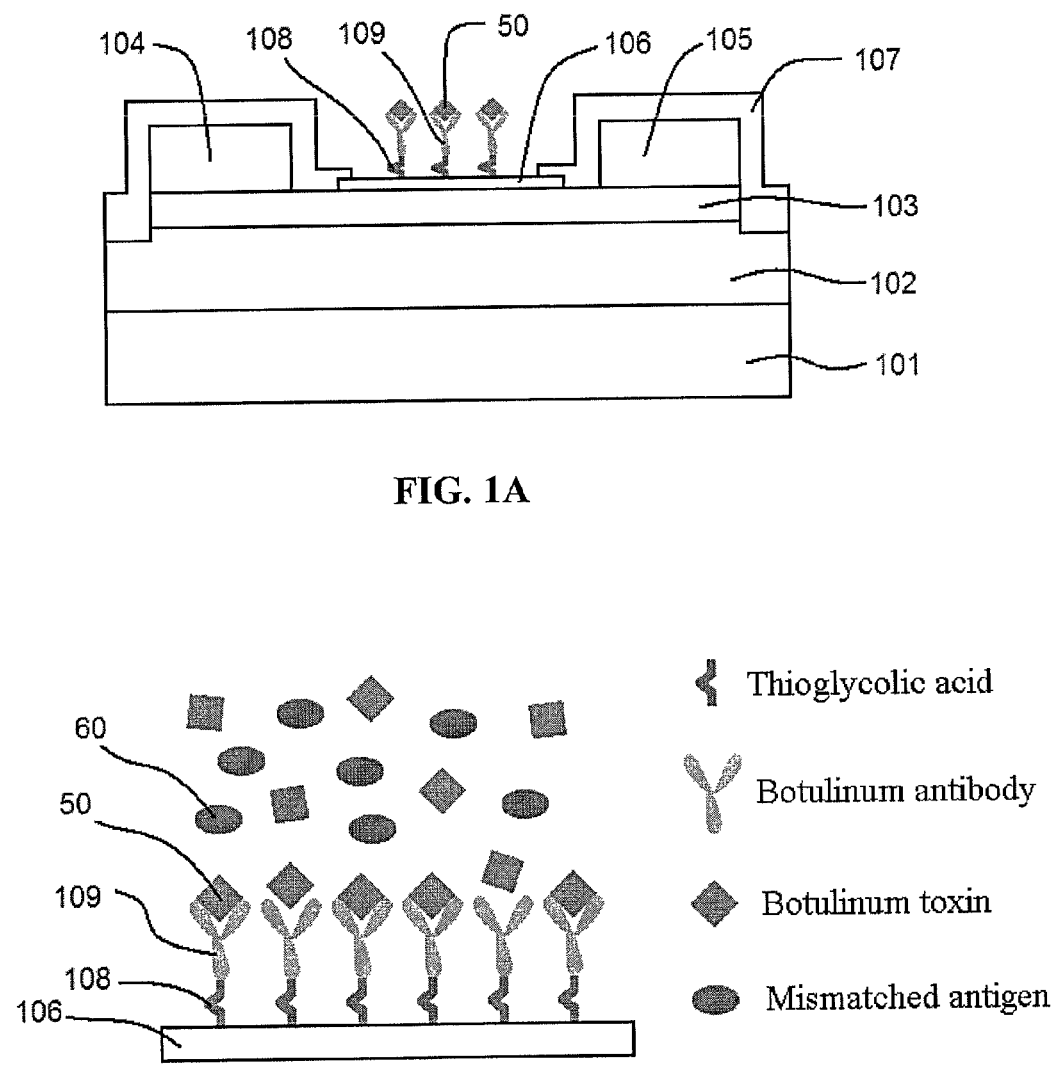

Referring to FIG. 1A, a botulinum toxin sensor can include an AlGaN/GaN HEMT grown on a substrate 101. The substrate 101 may be, for example, a silicon, sapphire, or SiC substrate. In one embodiment, epi-layers for the HEMT (e.g., the GaN 102 and AlGaN 103 layers) can be grown by molecular beam epitaxy (MBE) on the sapphire or SiC substrate. In another embodiment, the epi-layers can be grown by metal organic chemical vapor deposition (MOCVD) on the silicon, sapphire, or SiC substrate. Source and drain electrodes 104 and 105 can be provided, and an electrode 106 can be formed on the gate region of the HEMT. The electrode 106 can include a gold (Au) thin film. A protective layer 107 can be formed on the HEMT while exposing the gate region. The protective layer 107 can be formed of poly(methyl methacrylate) (PMMA). Then, a botulinum antibody coating 109 can be provided on the electrode 106. Although the binding molecule is described here as a botulinum antibody coating 109, any binding molecule that binds specifically to the botulinum toxin may be used. The gold surface can be functionalized with a bi-functional molecule 108, such as thioglycolic acid, before coating with the botulinum antibody. The thioglycolic acid can be immobilized by the strong interaction between the gold and the thiol-group of the thioglycolic acid.

Other binding (or linking) agents, such as cysteamine ($NH_2CH_2CH_2SH$), 1,2-ethanedithiol ($HSCH_2CH_2SH$), dimercaprol (BAL), diaminoethanetetraacetic acid (EDTA), 2,3-bis-sulfanylbutanedioic acid (DMSA), or 2,3-dimercapto-1-propanesulfonic acid (DMPS) can be utilized in certain embodiments.

In operation, any slight changes in the ambient of the HEMT affect the surface charges on the AlGaN/GaN. These changes in the surface charge are transduced into a change in the concentration of the 2DEG in the AlGaN/GaN HEMTs, leading to the decrease in the conductance for the device after exposure to botulinum toxin. FIG. 1B shows a detailed view of the gate electrode of a botulinum toxin sensor in accordance with an embodiment of the present invention. Referring to FIG. 1B, the botulinum antibody/antigen (109) on thioglycolic acid (108) functionalized Au-coated (106) gate area is selective to botulinum toxin 50 while avoiding mismatched antigen 60.

A HEMT with the botulinum antibody/antigen on thioglycolic acid functionalized Au-coated gate area can exhibit noticeable changes in the surface charges upon exposing the gate region to various concentrations of botulinum toxin, including sensing concentrations of about 1 ng/ml.

Although an AlGaN/GaN HEMT is described as the HEMT for use in the aforementioned embodiments, other HEMTs, such as an AlGaAs/GaAs HEMT, an InGaP/GaAs HEMT or an InAlAs/InGaAs HEMT can be used in place of the AlGaN/GaN HEMT.

In certain applications, the sensor can be provided to the environment under test through a passive step such as allowing the functionalized gate region to be exposed to samples in a surrounding ambient environment, or by an active step such as contacting a sample to the functionalized gate region.

In one embodiment, multiple sensors can be fabricated on a single chip by forming a plurality of HEMTs and then individually functionalizing each HEMT for a particular sensing application using any known masking techniques. Other circuitry can also be included, if needed.

According to one embodiment of the present invention a detection instrument is provided utilizing biological analyte-functionalized HEMT sensors. According to one implementation, a medical diagnostic and/or detection instrument is provided that enables the identification of biological material from fluid samples by HEMT-based sensor response to antigens that bind with antibody material immobilized on the gate region of a HEMT.

In one embodiment, the subject invention provides a system including multiple HEMT-based sensors for analyzing fluid samples for antigen content, and an electronic processor controlling and communicating the sensors with monitoring and processing electronics. The subject system can be incorporated in a hand held device where the sensors are configured within a removable sensor cartridge and a cartridge reader, user interface, and fluidic interface for sample delivery across cartridge sensors are provided within a housing configured to receive the cartridge. The electronic processor and the monitoring and processing electronics may be disposed within the housing.

The cartridge for the sensors can be formed of plastic. In an embodiment, the cartridge may be formed of any suitable material capable of being molded around the sensors and electronic substrate. In a further embodiment, the cartridge may be designed for high volume production and can include embedded marking that can be read by the system upon introducing the cartridge to the housing configured to receive the cartridge. Serialization and configuration can be passed to the system for processing upon being read. In certain embodiments, the marking system can incorporate a bar code, and the system can incorporate a bar code reader. In one embodiment, RF tags or a wire may be embedded in the cartridge to enable automated use and tracking Custom configured cartridges can be provided according to application in order to provide configuration data for the control and reduction of error in use.

The electronic substrate can be configured to connect signal path to system interface for processing signals from multiple sensors.

The cartridge can be used to provide fluidic path for samples to be presented across the functionalized region of a sensor within the cartridge. The fluidic path may be across each sensor. In another embodiment, the fluidic path can be sensor-selective such that only a selected sensor or sensors will receive the fluid samples.

The cartridge may be suitable for bodily fluids as well as aqueous sample material created by introducing swab or wipe material into buffer fluid.

According to an embodiment, the cartridge can be used in the manufacturing process to provide a stable fixture for applying antibody material to each sensor active area when functionalizing the HEMT in batch production.

Multiple cartridges can be packaged in protective enclosures for storage or transporting the cartridges. The enclosure can include temperature and time monitoring devices to maximize the longevity of stored cartridges and maintain a history of storage temperature for traceability.

In one application, patients can be tested for bacterial infections (such as MRSA) and results of the tests provided in less than a minute. Accordingly, treatment can be started sooner, and a larger number of patients entering a hospital or healthcare facility can be screened.

Clinical diagnostic instruments can be provided for infectious disease factor identification and portable or fixed detection instruments can be provided for the detection of biological agents, which may be found as contaminants in food and other processes or used as weaponized material.

Advantageously, certain embodiments of the present invention provide small size, ease of operation, and low cost solutions for highly sensitive, accurate and fast resolution of biological toxin, bacterial, and viral identification. The subject HEMT-based sensors can be provided as custom configured removable cartridge assemblies.

It should be understood that the examples and embodiments described herein are for illustrative purposes only and that various modifications or changes in light thereof will be suggested to persons skilled in the art and are to be included within the spirit and purview of this application. The following examples should not be construed as limiting. All percentages are by weight and all solvent mixture proportions are by volume unless otherwise noted.

EXAMPLE 1

The HEMT structures used for the following examples have a 3 μm thick undoped GaN buffer, a 30 Å thick $Al_{0.3}Ga_{0.7}N$ spacer, and a 220 Å thick Si-doped $Al_{0.3}Ga_{0.7}N$ cap layer. Here, the epi-layers were grown by a molecular beam epitaxy system (MBE) on sapphire substrates. Mesa isolation was performed by an Inductively Coupled Plasma (ICP) etching with $Cl_2$/Ar based discharges at −90 V dc self-bias, ICP power of 300 W at 2 MHz and a process pressure of 5 mTorr. Ohmic contacts, each having an area of $10 \times 50$ μm$^2$ and separated with gaps of 5 μm, were formed of e-beam deposited Ti/Al/Pt/Au patterned by lift-off. The contacts were annealed at 850° C. for 45 sec under flowing $N_2$. A thin layer of Au was deposited on the gate region. A 400-nm-thick 4% Poly(methyl methacrylate) (PMMA) was used to encapsulate the source/drain regions, with only the gate region open to allow the liquid solutions to cross the surface.

The Au gated surface of the HEMT was functionalized with thioglycolic acid. A self-assembled monolayer of thioglycolic acid, $HSCH_2COOH$, an organic compound and containing both a thiol (mercaptan) and a carboxylic acid functional group, was anchored on the Au surface in the gate area through strong interaction between the gold and the thiol-group of the thioglycolic acid. The devices were first placed in the oxygen plasma chamber and then submerged in 1 mM aqueous solution of thioglycolic acid at 4° C. This resulted in binding of the thioglycolic acid to the Au surface in the gate area with the COOH groups available for further chemical linking of other functional groups. The device was incubated in a phosphate buffered saline (PBS) solution of 200 μg/ml botulinum polyclonal rabbit antibody for 18 hours before real time measurement of botulinum toxin subtype A acquired from Metabiologics Inc.

Figures 2, 3:
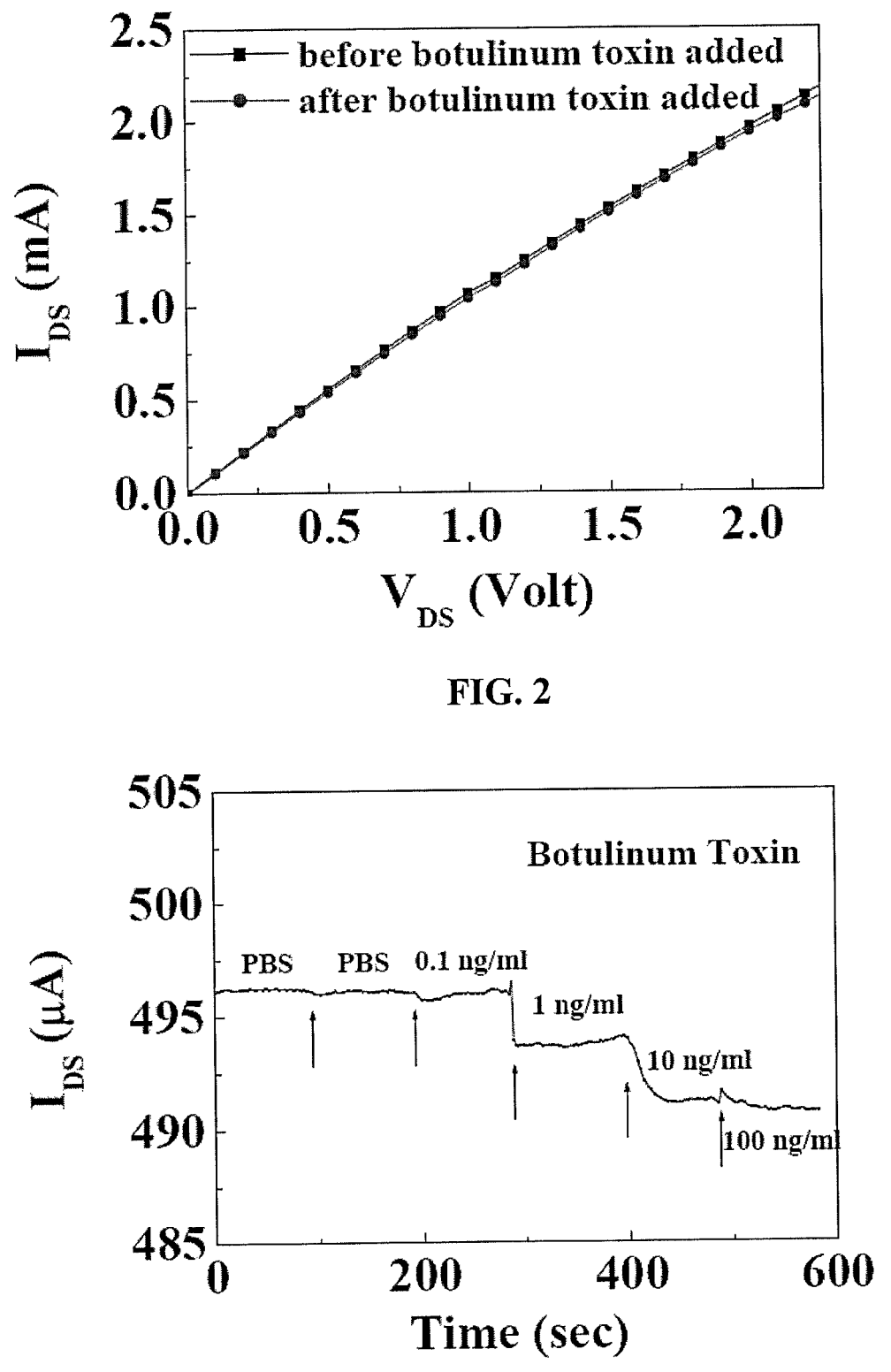

After incubation with a phosphate buffered saline (PBS) solution containing botulinum antibody at a concentration of 200 μg/ml, the device surface was thoroughly rinsed off with PBS and dried by a nitrogen blower. FIG. 2 shows a plot of I-V characteristics of the HEMT before and after exposure to botulinum toxin. The source-drain current-voltage characteristics were measured at 25° C. using an Agilent 4156C parameter analyzer with the gate region exposed. The source and drain current from the HEMT were measured before and after the sensor was exposed to 100 ng/ml of botulinum toxin at a constant drain bias voltage of 500 mV. Any slight changes in the ambient of the HEMT affect the surface charges on the AlGaN/GaN. These changes in the surface charge are transduced into a change in the concentration of the 2DEG in the AlGaN/GaN HEMTs, leading to the decrease in the conductance for the device after exposure to botulinum toxin.

FIG. 3 shows a real time botulinum toxin detection in PBS buffer solution using the source and drain current change with constant bias of 500 mV. Effectively no current change can be seen with the addition of buffer solution at around 100 seconds, showing the specificity and stability of the device. In clear contrast, the current change showed a rapid response in less than 5 seconds when target 1 ng/ml botulinum toxin was added to the surface of the PBS buffer solution. The abrupt current change due to the exposure of botulinum toxin in a buffer solution was stabilized after the botulinum toxin thoroughly diffused into the buffer solution. Different concentrations (from 0.1 ng/ml to 100 ng/ml) of the exposed target botulinum toxin in a buffer solution were detected. The example sensor saturates above 10 ng/ml of the toxin. The experiment at each concentration was repeated four times to calculate the standard deviation of source-drain current response. The limit of detection of the example device was below 1 ng/ml of botulinum toxin in PBS buffer solution.

Figures 4, 5:
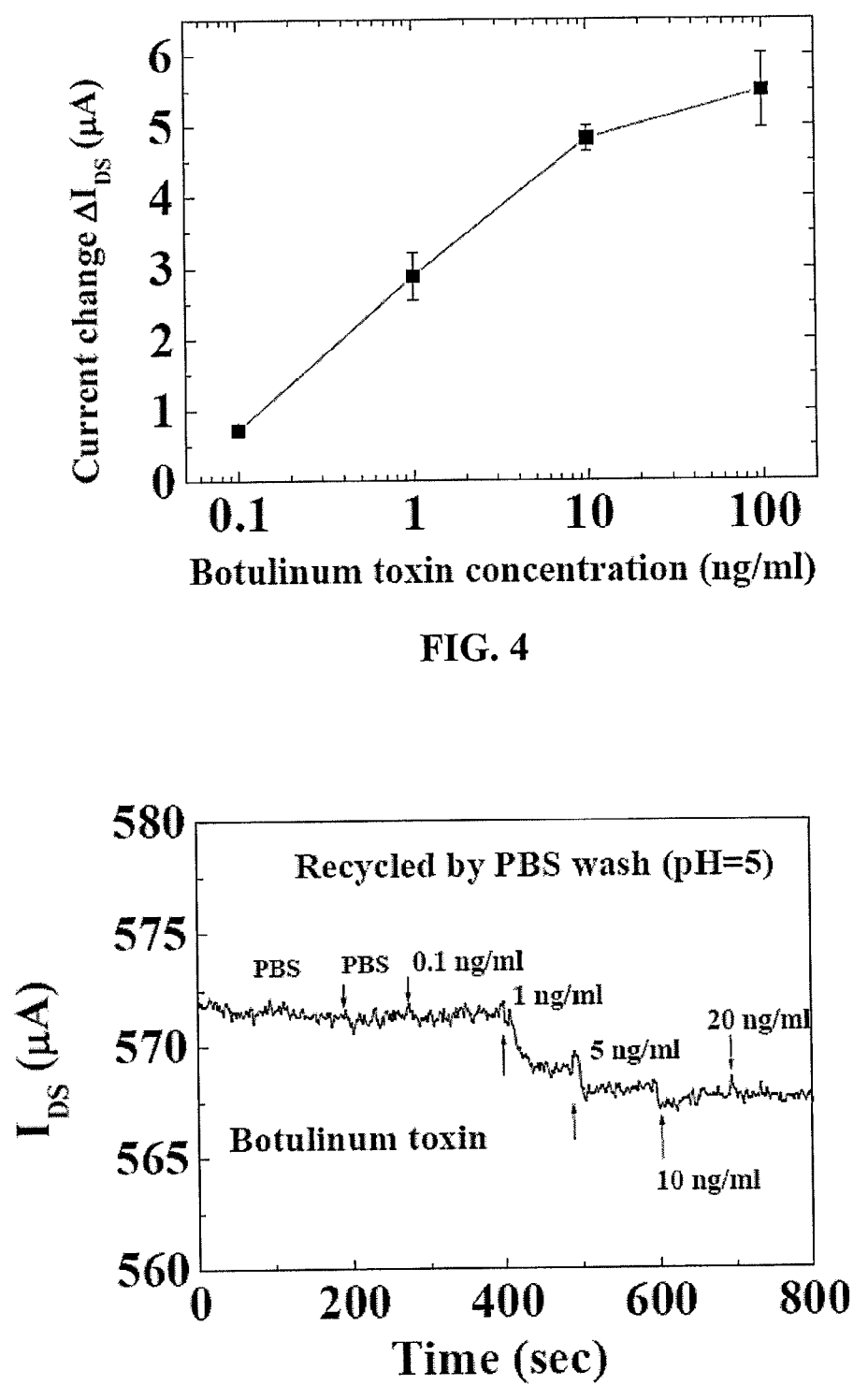

As shown in FIG. 4, the source-drain current change was nonlinearly proportional to botulinum toxin concentration.

FIG. 5 shows a real time test of botulinum toxin at different toxin concentrations with intervening washes to break antibody-antigen bonds. This result demonstrates the real-time capabilities and recyclability of the chip.

In summary, through a chemical modification method, the Au-gated region of an AlGaN/GaN HEMT structure can be functionalized for the detection of botulinum toxin with a limit of detection less than 1 ng/ml.

This electronic detection of bio-molecules is a significant step towards a field-deployed sensor chip, which can be integrated with a commercial available wireless transmitter to realize a real-time, fast response and high sensitivity botulinum toxin detector.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

What is claimed is:

1. A method of detecting botulinum, comprising:
preparing a cartridge including a high electron mobility transistor (HEMT) botulinum toxin sensor comprising a layer of gold on a gate region, thioglycolic acid anchored to a surface of the layer of gold, botulinum antibodies linked to the thioglycolic acid, and a fluidic path across the layer of gold on the gate region of the HEMT;
providing the fluidic path with a sample; and
generating a signal indicating detection of botulinum,
wherein the HEMT is configured to be removable from the cartridge, and
wherein the signal is generated by the sensor upon exposure of the botulinum antibodies to an amount of botulinum by transducing a change of a surface charge of the HEMT into a change in a concentration of two-dimensional electron gas in the HEMT.

2. The method according to claim 1, further comprising wirelessly transmitting the signal generated by the sensor to a monitoring device.

3. The method according to claim 1, wherein the signal is a source-drain current ($I_{DS}$) of the HEMT at a constant drain bias voltage.

4. The method according to claim 1, wherein the HEMT is configured to output the signal according to conductive operation of charge carriers controlled by the surface charge indicative of the amount of the botulinum binding to the botulinum antibodies.

5. The method according to claim 1, wherein the amount of botulinum to initially generate the signal is about 1 ng/ml.

* * * * *